United States Patent [19]

Imai et al.

[11] Patent Number: 5,773,662

[45] Date of Patent: Jun. 30, 1998

[54] AUTOMATIC ANALYZING METHOD USING A PLURALITY OF REAGENTS AND APPARATUS THEREFOR

[75] Inventors: Kyoko Imai; Isao Shindo, both of Hitachinaka; Kahei Shiraishi, Hitachioota, all of Japan

[73] Assignee: Hitachi, Ltd., Tokyo, Japan

[21] Appl. No.: 705,733

[22] Filed: Aug. 30, 1996

[30] Foreign Application Priority Data

Sep. 5, 1995 [JP] Japan ................................. 7-227980

[51] Int. Cl.⁶ ............................................. G01N 35/02
[52] U.S. Cl. .............................. 436/50; 436/47; 436/49; 422/64; 422/67
[58] Field of Search ............................ 422/63, 64, 67; 436/43, 47, 49, 50, 55, 174, 180; 364/497

[56] References Cited

U.S. PATENT DOCUMENTS

| | | | |
|---|---|---|---|
| 4,276,258 | 6/1981 | Ginsberg et al. | 422/64 |
| 4,908,186 | 3/1990 | Sakamaki | 422/64 |
| 4,908,320 | 3/1990 | Zakowshi et al. | 436/45 |
| 5,037,612 | 8/1991 | Takahashi et al. | 422/64 |
| 5,434,083 | 7/1995 | Mitsumaki et al. | 436/48 |

FOREIGN PATENT DOCUMENTS

| | | |
|---|---|---|
| 0316766 | 5/1989 | European Pat. Off. . |
| 59-22905 | 5/1984 | Japan . |
| 6-103311 | 12/1994 | Japan . |

*Primary Examiner*—Long V. Le
*Attorney, Agent, or Firm*—Fay, Sharpe, Beall, Fagan, Minnich & McKee

[57] ABSTRACT

In an automatic analyzing apparatus for analyzing multi-analysis items in regard to biological samples, a reaction disk, on which a lot of reaction containers are arranged, is repeatedly rotated by one rotation plus one pitch and stopped for receiving a reagent, and intermediately pauses twice between the stops without delivering reagents. The apparatus is so set that a third reagent for the latest delivery timing is delivered during a stop for receiving a sample at a single reagent delivering position E, and a first and a second reagent are delivered during the intermediate pauses at the single reagent delivering position E. After delivering a sample to a specified reaction container, the reaction container is delivered with the first reagent during an intermediate pause in a first cycle and the second reagent during an intermediate pause in a cycle after the delivery of the first reagent, and then the third reagent during a stop for receiving a sample in a cycle after the delivery of the second reagent.

7 Claims, 2 Drawing Sheets

AUTOMATIC ANALYZING METHOD USING A PLURALITY OF REAGENTS AND APPARATUS THEREFOR

BACKGROUND OF THE INVENTION

The present invention relates to a method and an apparatus for automatically analyzing biological samples and, more particularly, to a method and an apparatus for analyzing multi-analysis items through biochemical assay or immunoassay.

An example of an automatic analyzing apparatus of random access type is disclosed in Japanese Patent Publication No. 59-22905. In the automatic analyzing apparatus of random access type, analysis of multi-analysis items is performed by arranging a lot of reaction vessels or containers on a single reaction line. The analyzer in this prior art has two reagent pipetting mechanisms for a first reagent and a second reagent. That is, the first reagent for each analysis item is delivered to the reaction containers using one of the reagent pipetting mechanisms, and the second reagent for each analysis item is delivered to the reaction containers using the other of the reagent pipetting mechanisms.

On the other hand, an analyzer for multi-analysis items having a single reagent pipetting mechanism is disclosed in Japanese Patent Publication No. 06-103311. In the analyzer, one machine unit cycle is defined as a period from a precedent sample delivery to a row of reaction vessels or containers arranged on a reaction disk to the following sample delivery. During a unit cycle between a pause of transferring the row of reaction containers for receiving samples in the preceding unit cycle and a pause of transferring the row of reaction containers for receiving samples in the following unit cycle, the rotating operation of the reaction disk is so controlled as to be stopped plural times without receiving any samples in the middle of the unit cycle of transferring the row of reaction containers. When the reaction disk is stopped to receive samples, a first reagent corresponding to an analysis item for the previously received samples is delivered to the reaction containers.

Further, in the analyzer of Japanese Patent Publication No. 06-103311, when the reaction disk is stopped to receive samples, the position for receiving reagents is arranged near the position for receiving samples. That is, both of the reaction containers to receive reagents and the reaction containers to receive samples are adjacent to each other. However, in the case where the position for receiving reagents is arranged near the position for receiving samples, there arises a disadvantage in that the sample pipetting mechanism and the reagent pipetting mechanism mechanically interact to hit each other because both of the sample pipetting mechanism and the reagent pipetting mechanism are constructed so as to revolve their arms for supporting a nozzle.

Furthermore, in the analyzer of Japanese Patent Publication No. 06-103311, the position for receiving reagents is separately provided from the stirring position. However, it is not preferable for progress of the reaction to separately provide the position for receiving reagents from the stirring position because a sample and a reagent are stirred at a certain time after the sample and the reagent are delivered.

SUMMARY OF THE INVENTION

An object of the present invention is to provide an analyzing method and an analyzing apparatus in which more than two kinds of reagents can be delivered to the same reaction vessel or container using a single reagent pipetting mechanism, and the position for receiving reagents can be provided separately from the position for receiving sample, and sample reagents can be delivered to a row of reaction containers without disturbing the progress of the reaction.

Another object of the present invention is to provide an analyzing method and an analyzing apparatus in which reaction containers having different reaction times corresponding to the kinds of analysis items can be arranged on the same row of reaction vessels or containers.

The present invention can be applied to an analyzing apparatus in which a row of reaction vessels or containers arranged in a loop-shape is transferred during a unit cycle from a preceding sample delivery to the following sample delivery to the row of reaction containers in such a manner that a plurality of the reaction containers pass across a light beam of a photometer, intermediate pauses of transferring the row of reaction containers being made without delivering any samples in the middle of the unit cycle, and a reagent being delivered to the reaction containers at a single reagent delivering position provided in the middle of the transfer path of the row of reaction containers.

When the row of reaction containers is stopped to deliver a sample, a sample is delivered to a reaction container at a sample delivering position, and a reagent to be delivered last among reagents for multi-analysis items using the most kinds of reagents is delivered to a reaction vessel or container at the reagent delivering position, and during the intermediate pause a first reagent to produce a first reaction of a sample to be analyzed is delivered to a reaction vessel or container at the reagent delivering position.

In a preferable embodiment, the content of the reaction container pausing at the reagent delivering position is stirred after delivering a reagent to another reaction vessel or container pausing at the reagent delivering position. The analyzing apparatus is set so that the reagent to be delivered last is a third reagent, and a reaction time for an analysis item using the first, the second and the third reagents is set to substantially twice as long as a reaction time for an analysis item using the first and the third reagents. It is preferable that a plurality of intermediate pauses of the row of reaction containers are made, the third reagent is delivered to the reaction container for an analysis item using the first, the second and the third reagents positioned at the reagent delivering position during a pause of transferring the row of reaction containers to deliver a sample for the other analysis item, and the second reagent is delivered to the reaction container positioned at the reagent delivering position during one of the intermediate pauses. When a specified reaction container corresponding to a specified analysis item not requiring the second and the third reagents is stopped in order to deliver a sample for the other analysis item, no reagent is not delivered to the specified reaction container even if the specified reaction container is positioned at the reagent delivering position.

DETAILED DESCRIPTION OF THE PREFERRED EMBODIMENTS

Figure 1:
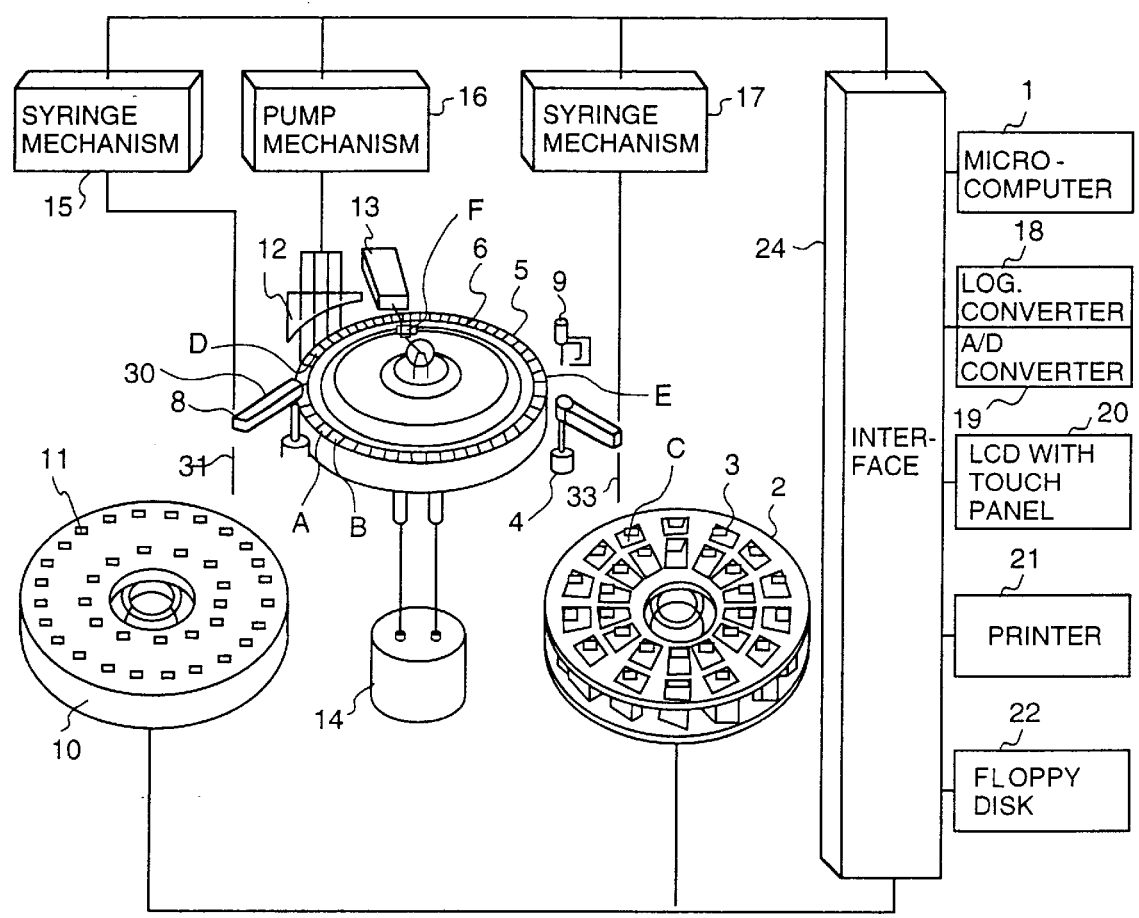
FIG. 1 is a schematic view showing an embodiment of an automatic biochemical analyzing apparatus in accordance with the present invention.

An analyzing apparatus shown in FIG. 1 is an apparatus for reacting a sample of blood serum with desired reagents on a reaction line. A row of reaction vessels or containers 6 on a reaction disk 5 are repeatedly rotated in a period from the preceding sample delivery to the following sample delivery as a machine unit cycles. During each of the cycle, the row of reaction containers is transferred by a transferring mechanism using a step motor or the like in such a manner that the plurality of reaction containers 6 pass across a light beam of a photometer 13.

The rotation of the reaction disk 5 is stopped when every time when a sample is received at a sample receiving position A. During a unit cycle, the row of reaction containers is transferred by an angle corresponding to a plurality of reaction vessels or containers. The transfer angle in one cycle may be one rotation plus one pitch, or one rotation minus one pitch, or one-half rotation plus one pitch.

In the middle of each of the cycles, a micro-computer 1 as a controller controls so that transfer of the row of reaction containers is stopped without any sample delivery. In the transfer path of the row of reaction containers, there are provided a sample receiving position A, a vessel or container cleaning position D, a reagent receiving position E, a light measuring position F and so on. A sample delivering station is in the sample receiving position A, and a reagent delivering station is in the reagent receiving position E. A single reagent pipetting mechanism 4 works as a reagent delivering apparatus.

When the row of reaction containers is stopped to be for sample delivery, the micro-computer 1 controls the operation of the reagent pipetting mechanism 4 and the reagent disk 2 so as to deliver a reagent to be delivered last in order among reagents for an analysis item using the most kinds of reagents to a reaction vessel or container at the reagent receiving position E. When the row of reaction containers is intermediately stopped, the micro-computer 1 controls the operation of the reagent pipetting mechanism 4 and the reagent disk 2 so as to deliver a first reagent to produce a first reaction to a reaction vessel or container at the reagent receiving position E.

The number of kinds of the reagents required for measuring an analysis item depends on a kind of the analysis item. In regard to a certain analysis item, a first reagent is a reagent to be delivered first for a first reaction with a sample, and a second reagent is a reagent to be delivered second for a second reaction with the sample, a third reagent is a reagent to be delivered third for a third reaction with the sample, and a fourth reagent is a reagent to be delivered fourth for a fourth reaction with the sample.

Figure 2A:
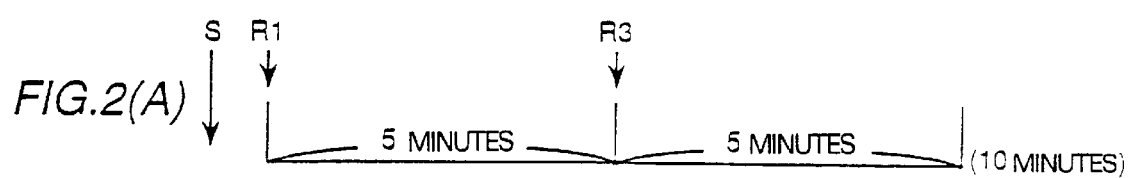
FIG. 2 (A), FIG.2 (B) and FIG. 2 (C) are charts showing examples of reaction progressing patterns.
Figure 2B:
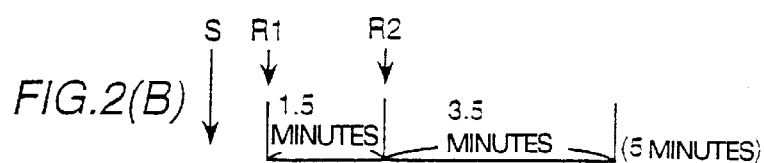
Figure 2C:
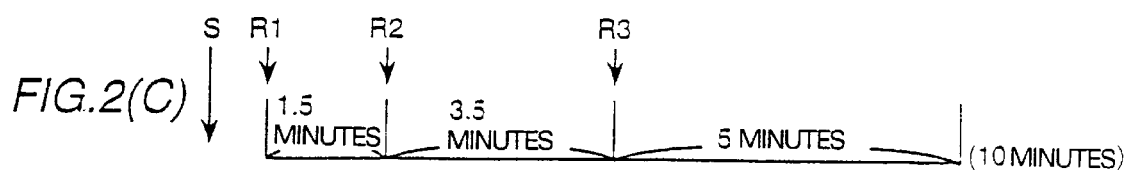

In a case where an analyzer is so programmed as to perform a process of a three-reagent analysis item, the analyzer may have reaction patterns as shown in FIG. 2 (A), FIG. 2 (B) and FIG. 2 (C). Referring to the figures, the reference character S indicates a sample, the reference character R1 indicates a reagent to be delivered at the first timing, the reference character R2 indicates a reagent to be delivered at the second timing, and the reference character R3 indicates a reagent to be delivered at the third timing.

FIG. 2 (A) shows a reaction progress pattern of a two-reagent analysis item, and the total reaction time is 10 minutes. FIG. 2 (B) also shows a reaction progress pattern of a two-reagent analysis item, but the total reaction time is 5 minutes. FIG. 2 (C) shows a reaction progress pattern of a three-reagent analysis item, and the total reaction time is 10 minutes. The total reaction time of FIG. 2 (C) is set twice as long as the total reaction time of FIG. 2 (B).

The operation of the embodiment of FIG. 1 will be described below, referring to FIG. 2 (A), FIG. 2 (B) and FIG. 2 (C). The reaction disk 5 of turn-table type holding 48 transparent reaction vessels or containers rotates one rotation plus one reaction container distance (pitch) during one machine unit cycle. During the middle of the rotation of one rotation plus one pitch, there are provided three pausing periods; that is, so-called divisional rotation is performed. A reaction vessel or container is stopped at the predetermined reagent delivering position E so that the first reagent, the second reagent or the third reagent may be delivered during each of the pausing periods in the cycle. The rotation of the reaction disk 5 is controlled so that the reaction container arrives at the reagent delivering position E at a reagent delivering timing R3 for the last delivery within a predetermined reagent delivering timing by transferring the reaction container having been delivered with a sample by one rotation plus one pitch. The reagent disk 2 holding a plurality of reagents (up to the third reagent) for respective measuring items at predetermined positions is controlled so as to stop at a predetermined reagent pipetting position C for pipetting necessary reagents corresponding to the operation of the reaction disk 5. In synchronism with these, the single reagent pipetting mechanism 4 having a pipetting probe 33 moving between the reagent pipetting position C and the reagent delivering position E is operated. Absorbencies of all necessary reaction containers 6 are measured for every cycle during the dividing rotation of every cycle of the reaction disk 5.

In the apparatus of FIG. 1, 48 transparent rectangular reaction containers 6 are held on a rotating reaction disk 5 in a loop-shape. The reaction containers 6 are made of a plastic or a glass. In more detail, the reaction containers 6 are arranged in the circular periphery around the rotating center of the reaction disk 5 to form a row. Therefore, when the reaction disk 5 is rotated, the row of reaction containers 6 is moved in the direction of the row, that is, along the circular periphery around the rotating center of the reaction disk 5. Forty reagent containers 3 are arranged on a rotating reagent disk 2. Sample cups for 35 samples to be analyzed and 22 reference samples are mounted on a rotating sample disk 10.

A desired amount of each sample liquid based on input of analyzed sample information from the sample container placed on a predetermined position on the sample disk 10 is sucked into a nozzle 31 held by a movable arm 30 and delivered to a reaction container 6 at the sample delivering position A. In order to do so, a simple sampling mechanism 8 and a micro-syringe mechanism 15 are provided. The single reagent pipetting mechanism 4 and a syringe mechanism 17 are revolved based on sample analyzing information input by an operator. A desired amount of a reagent based on the input information is sucked from a reagent container (bottle) at a reagent sucking position C on the stopped reagent disk 2 into a reagent nozzle 33 held by a movable arm 32, and delivered into a reaction container 6 at the reagent delivering position on the reaction disk. A position for stirring the reaction liquid produced in the reaction container using the stirring mechanism 9 agrees with the reagent delivering position E on the reaction disk 5.

The analyzer further comprises a multi-wavelength photometer 13 for measuring absorbance of each reaction container passing across a light beam with a predetermined wavelength based on input information during rotation of the reaction disk 5, a cleaning mechanism 12 and a cleaning water feed and drain pump mechanism 16 for cleaning a reaction vessel or container after completion of measurement, a LOG converter 18, an A/D converter 19, a computer 1 for controlling the operation of each of the mechanisms and for processing data, an output printer 21, an LCD 20 with touch panels for input/output and display, a floppy disk mechanism 22 for program, measuring condition and data storage, a constant temperature bath 14 of recirculation type for maintaining each of the reaction containers on the reaction disk at a constant temperature, and an interface 24 for connecting the computer 1 to each of the mechanisms.

At the start of measuring using the apparatus of FIG. 1, an operator initially sets reference samples if necessary and measured samples onto the sample disk 10 and inputs measuring items for individual sample liquids, that is, analysis item selecting information. Further, the operator sets reagents necessary for the measuring onto the reagent disk 2. The measuring conditions for each of the measuring items is supplied by a floppy disk 22. Table 1 shows an examples of measuring conditions.

TABLE 1

|  | MEASURING CONDITION | | |
| --- | --- | --- | --- |
| SCREEN INFORMATION | TP |  | BIL |
| ANALYSIS ITEM |  | AST |  |
| ASSAY METHOD | END POINT | RATE | END POINT |
| AMOUNT OF SAMPLE ($\mu l$) | 5 | 12 | 5 |
| AMOUNT OF FIRST REAGENT ($\mu l$) | 270 | 250 | 150 |
| AMOUNT OF SECOND REAGENT ($\mu l$) | 0 | 75 | 200 |
| AMOUNT OF THIRD REAGENT ($\mu l$) | 0 | 0 | 100 |
| FIRST REAGENT SET POSITION | 1 | 2 | 4 |
| SECOND REAGENT SET POSITION | 0 | 3 | 5 |
| THIRD REAGENT SET POSITION | 0 | 0 | 6 |
| MAIN WAVELENGTH (nm) | 700 | 376 | 660 |
| SUB-WAVELENGTH (nm) | 546 | 340 | 660 |

Measuring conditions input from the LCD 20 with touch panel and displayed on the screen include a calculating condition of absorbance of the reagent reaction liquid (assay method in the table), delivered amount of sample (amount of sample in the table), delivering condition of the first reagent, the second reagent and the third reagent (amount of reagent, position on the reagent disk on which each of the reagent is set, in the table), measuring wavelength (main wavelength, sub-wavelength, in the table), concentration of the reference liquid, and K-factor, as shown in Table 1.

As shown in Table 1, the apparatus can perform a one-liquid method using only the first reagent as shown by TP, a two-liquid method using the first and the second reagents as shown by AST, and a three-liquid method using the first, the second and the third reagents as shown by BIL. It is also possible to perform a two-liquid method using the first reagent and the third reagent, which is delivered at the timing of the second reagent, though it is not shown in the example.

After completion of the above preparation, the operator sets to start the apparatus. As the apparatus is started, the reaction disk 5 and the sample disk 10 are rotated, and a sample cup 11 of a sample liquid (a reference liquid or an analyzed sample) to be measured first and a clean reaction vessel or container 6 to be used first are positioned at predetermined positions of the individual disks 10, 5. In this state, a proper amount (amount of sample shown in the table) of the sample to an analysis item to be measured first is pipetted from the sample cup 11 into the reaction container 6 by operation of the sample pipetting mechanism 8 and the micro-syringe mechanism 15.

Then the reaction disk 5 is rotated counterclockwise according to a predetermined operation which will be described later. The reaction container delivered with the sample is rotated by one rotation plus one pitch (one reaction container distance) to be moved from a position A and stopped at a position B after one machine cycle, and then operation of the next cycle is started. That is, the reaction disk 5 is stopped at a position advancing by one pitch in the counterclockwise direction every starting of the operation (machine) cycle (in this embodiment, one cycle is 18 seconds, that is (200 tests/hour), and the next sample liquid is delivered in the reaction container at the position A neighboring in the left hand side. During rotating of the reaction disk 5, absorbencies of all the reaction containers passing across the light beam of the photometer 13 are measured. In other words, the absorbencies of all the 48 reaction containers are measured every cycle by each wavelength corresponding to each of the analysis items based on the input information.

Further, in order to attain the object of the present invention, some design idea is necessary for the rotating operation of the reaction disk 5 in each of the cycles. That is, during one cycle in which the reaction disk is rotated counterclockwise by one rotation plus one pitch, three pauses at proper timings and at proper positions are provided to add and mix the first, the second and the third reagents necessary for each of the reaction containers, therefore, necessary for each of the analysis items, by cooperatively operating the reagent pipetting mechanism 4, the syringe mechanism 17 and the stirring mechanism 9. Time loss consumed for pausing of the reaction disk is reduced by setting one of the three pauses to the starting time of each cycle, that is, the sample delivering timing in common.

Further, analysis can be speedily performed by delivering the third reagent (R3) to be delivered at the latest timing in the predetermined whole reaction progressing pattern in the analyzer to the reaction container at the predetermined reagent delivering position during a pause of the reaction disk for delivering a sample.

That is, in order to realize an analyzer in which the number of rotations of the reaction disk is reduced as much as possible, the rotating operation of the reaction disk is so controlled that a reagent to be delivered at the latest reagent delivering timing in the predetermined whole reaction progressing pattern, not the first reagent for the analysis item, is delivered into a predetermined reaction vessel or container at the reagent delivering position E during a pause of the reaction disk 5 for delivering a sample. For example, as to a three-reagent analysis item, in a case where there are three reagent delivering timings (0 minute, 1.5 minutes and 5 minutes after initiation of reaction as shown in FIG. 2). the third reagent (R3) to be delivered at the latest reagent delivering timing of 5 minutes is delivered to the predetermined reaction container at the reagent delivering position during a pause of transfer for receiving a sample. In a case of an analysis item using only R1 and R2, the analysis can be completed in 5 minutes since delivering of R3 is unnecessary.

Rotation of the reaction disk is in close connection with the reaction progressing pattern. Therefore, the kinds of the reagents for the analysis items to be delivered to the reaction container at predetermined reagent delivering position during a pause of transfer for receiving a sample and number of reaction containers transferred from the sample delivering position to the reagent delivering position are determined based on the reaction pattern.

A method of delivering a sample and a reagent at a starting time of the analysis operation using the analyzing apparatus will be described below, focusing attention on a specified reaction vessel or container. In the starting time of the analyzing operation, the row of reaction containers has no samples at all. The specified reaction container is stopped at a position A in FIG. 1 at the first pause of transfer in the first cycle which corresponds the starting time of each of cycles described above, and an amount of a sample corresponding to the first analysis item for the above first sample is delivered to the specified reaction container. Until the second pause of the first cycle, the specified reaction container is further transferred at a predetermined position, advancing counterclockwise by 12 pitches. Before the third pause of the first cycle, the specified reaction container is further transferred at the reagent delivering position E, advancing counterclockwise by 5 pitches. The reagent disk 2 is controlled so that the bottle 3 of the first reagent corresponding to the analysis item is stopped at the reagent pipetting position (the position E in the figure) at the third pause. In this state, a certain amount of the first reagent is delivered to the specified reaction container by operation of the reagent pipetting mechanism 4 and the syringe mechanism 17. Further, during the third pause and after delivering the R1, the content of the reaction container is stirred at a predetermined position E by the stirring mechanism 9.

Then the specified reaction container is transferred according to the predetermined operation pattern. Before the first pause of the second cycle, the specified reaction container is transferred from a position A to a predetermined position B advancing counterclockwise by 1 pitch. 1.5 minutes after the first reagent delivery, that is, at the second pause of the sixth cycle, the specified reaction container is again stopped at the predetermined position E, and at the same time the reagent disk 2 is controlled so that the second reagent for the first analysis item is stopped at the pipetting position (the position C in the figure). In this state, a certain amount of the second reagent is delivered to the specified reaction container by operation of the reagent pipetting mechanism 4 and the syringe mechanism 17. Further, during the second pause, the content of the reaction container is stirred at a predetermined position E by the stirring mechanism 9.

3.5 minutes after the second reagent delivery, that is, at the first pause of the eighteenth cycle, the specified reaction container is again stopped at the predetermined position E, and at the same time the reagent disk 2 is controlled so that the third reagent for the first analysis item is stopped at the pipetting position C. In this state, a certain amount of the third reagent is delivered to the specified reaction container by operation of the reagent pipetting mechanism 4 and the syringe mechanism 17. Further, during the third pause, the content of the reaction container is stirred at a predetermined position E by the stirring mechanism 9.

As described above, in seeing only one of the first reaction containers, in the first cycle, the sample liquid and the first reagent are delivered in the reaction container and the reaction liquid is stirred to progress the first reaction. 1.5 minutes after delivering of the first reagent, that is, in the sixth cycle, the second reagent is delivered and the reaction liquid is stirred to progress the predetermined second reaction. 3.5 minutes after delivering of the second reagent in the eighteenth cycle, that is, in the latest reagent delivering time set in this embodiment (5 minutes after delivering of the first reagent), the third reagent is delivered and the reaction liquid is stirred to progress the predetermined third reaction. The reaction container passes across the light beam of the multi-wavelength photometer 13 every cycle, and the absorbance is measured with a wave length selected according to the analysis item based on the input information and the result is stored in the memory. Finally, after completion of measuring until the thirty-fifth cycle, that is, 10 minutes after delivering of the first reagent, at the first pauses of the thirty-eighth cycle to the forty-first cycle the specified reaction container is stopped at the cleaning position of the position D in FIG. 1 under the cleaning mechanism 12 to be cleaned. The cleaned reaction container is stopped at the position A at the first pause of the forty-ninth cycle and a sample liquid corresponding to the forty-ninth analysis item is delivered to the reaction container.

In the condition of delivering the reagent input for each analysis item described above, when the input value for the second reagent R2 and/or the input value for the third reagent R3 is 0 (zero), the second reagent or the third reagent is not delivered and the analysis method becomes a one-liquid method or/and a two-liquid method because the computer 1 controls the pipetting mechanism 4 so as to be not operated based on the zero input information even if the reaction container corresponding to the analysis item is stopped at the reagent delivering position E. Further, when only the input value of R2 is zero, it is possible to perform a two-liquid method of different delivering timing in which the second reagent is not delivered but the third reagent is delivered.

That is, when the reaction progressing patterns in FIG. 2 are combined, it is preferable that the reagent delivering position is set so as to agree with the transfer position of the reaction container for the reagent to be delivered at the latest timing among a plurality of predetermined reagent delivering timings, which results in the smallest loss in rotation of the reaction disk. Further, it is preferable that the reagent delivering position is set so as to agree with the stirring position of the reaction liquid.

Although the aforementioned embodiment can perform up to a three-liquid method at maximum, it is possible to realize a one-liquid method, a two-liquid method, a three-liquid method, a four-liquid method and a five-liquid method of different reaction times by setting number of transfer pauses in a cycle to 4 or 5 and by properly controlling the reagent delivering mechanism rotation, and stopping position of the reagent disk and the stirring mechanism.

Although the aforementioned embodiment is a very simple apparatus having the single reagent pipetting mechanism, the single reagent disk, the single reaction disk, the single sample pipetting mechanism and the single sample disk, the embodiment can freely cope with from a one-liquid method to a multi-liquid method and can employ a measuring system in which a plurality of reactions having different reaction time coexist. Further, since the reagent delivering system influencing the reliability of the total apparatus system is single, maintenance and inspection of the apparatus can be easily performed, and accordingly the reliability of the apparatus can be improved. At the same time the cost of the apparatus can be decreased.

As having been described above, an automatic analyzing apparatus for multi-analysis items can be provided. Even if analysis items requiring reagent delivery for a one-liquid method and analysis items requiring reagent delivery for a method of more than three liquids method are mixed on the same reaction container transfer path, the automatic analyzing apparatus does not disturb the periodical operation of the sample delivery to the reaction containers and can deliver the reagents necessary for the items by the single reagent pipetting mechanism, and can cope with the analysis items of reactions having different reaction times.

What is claimed is:
1. An analyzing method in which a row of reaction containers is cyclically transferred on a reaction line formed in a loop so as to have a unit transferring cycle that is defined between stoppages for successive sample additions, wherein the reaction containers are transferred so as to pass across a light beam of a photometer during the unit transferring cycle, and wherein the reaction line includes a sample adding position and a single reagent delivering position, the analyzing method comprising the steps of:

causing the row of reaction containers to make at least one intermediate pause during which no samples are delivered in the course of the unit transferring cycle, between said successive sample additions;

delivering a first reagent at the single reagent delivering position to a first reaction container containing a first sample during the at least one intermediate pause; and adding a second sample to a new reaction container at the sample adding position when the first reaction container containing the first sample and first reagent pauses at the single reagent delivering position to receive a final reagent for the first reaction container at the stoppage that ends the unit transferring cycle.

2. An analyzing method according to claim 1, wherein said final reagent is a third reagent, and a reaction time for an analysis item using the first reagent, a second reagent, and the third reagent is set to substantially twice as long as a reaction time for an analysis item using the first and the third reagents.

3. An analyzing method according to claim 1, further comprising the step of stirring the content of the first reaction container at said single reagent delivering position after delivering the first reagent to the first reaction container at said single reagent delivering position.

4. An analyzing method according to claim 2, wherein said causing step is performed to make a plurality of said intermediate pauses; and wherein the analyzing method further comprises the steps of delivering the third reagent to the first reaction container at said single reagent delivering position, for an analysis item using the first, second and third reagents, during a pause of transferring the row of reaction containers to deliver the second sample for another analysis item; and delivering the second reagent to the reaction container positioned at said single reagent delivering position at one of the intermediate pauses.

5. An analyzing method according to claim 4, wherein when a specified reaction container corresponding to a specified analysis item not requiring the second and the third reagents is stopped to permit a sample to be delivered for said another analysis item, no reagent is delivered to the specified reaction container even if the specified reaction container is positioned at said reagent delivering position.

6. An automatic analyzing apparatus, comprising:

means for transferring a row of reaction containers in such a manner that a plurality of the reaction containers pass across a light beam of a photometer during a unit cycle that is defined as extending between successive sample deliveries;

a controller for making at least one intermediate pause of transfer of said row of reaction containers during which no samples are delivered, in the middle of said unit cycle between said successive sample deliveries;

a single reagent delivering mechanism for delivering a reagent corresponding to each analysis item at a reagent delivering position in the middle of the transfer of said row of reaction containers; and reagent positioning means for positioning a reagent container containing a first reagent at a reagent sucking position during the at least one intermediate pause, and for positioning a reagent container containing a final reagent at the reagent sucking position during a pause for a subsequent sample delivery that ends said unit cycle;

wherein said controller controls said single reagent delivering mechanism so as to deliver said final reagent to be delivered last among all reagents for a multi-reagent analysis item to a reaction container at said reagent delivering position when said row of reaction containers is stopped to permit a sample to be delivered; and wherein said controller controls said single reagent delivering mechanism so as to deliver the first reagent to produce a first reaction of a sample to be analyzed to a reaction container at said reagent delivering position during said at least one intermediate pause.

7. An automatic analyzing apparatus according to claim 6, further comprising a stirring mechanism for stirring the content of the reaction container stopping at said reagent delivering position after a reagent has been delivered to said reaction container at said reagent delivering position.

\* \* \* \* \*